United States Patent [19]

Hasspacher et al.

[11] 4,094,987
[45] June 13, 1978

[54] 2-(3-M-HYDROXY-PHENYL-1-SUBSTITUTED-3-PYRROLIDINYL)-ETHANOLS

[75] Inventors: Klaus Hasspacher, Riehen; Michael Strasser, Binningen, both of Switzerland

[73] Assignee: Sandoz Ltd., Basel, Switzerland

[21] Appl. No.: 762,209

[22] Filed: Jan. 24, 1977

[30] Foreign Application Priority Data

Jan. 28, 1976 Switzerland .................. 1070/76
Jan. 28, 1976 Switzerland .................. 1071/76

[51] Int. Cl.$^2$ ................. C07D 207/44; A61K 31/40
[52] U.S. Cl. ..................... 424/274; 260/326.5 M; 260/326.5 D
[58] Field of Search ............... 260/326.5 D, 326.5 M; 424/274

[56] References Cited

U.S. PATENT DOCUMENTS 3,745,171  7/1973  Lockhart .............. 260/326.5 M

*Primary Examiner*—Jose Tovar
*Attorney, Agent, or Firm*—Gerald D. Sharkin; Robert S. Honor; Timothy G. Rothwell

[57] ABSTRACT

This invention provides compounds of formula I,

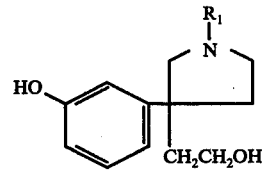

wherein
R$_1$ is alkyl of 4 to 8 carbon atoms; cycloalkyl of 4 to 6 carbon atoms; phenethyl or phenethyl monosubstituted in the phenyl residue with fluorine, chlorine, bromine, methoxy or alkyl of 1 to 4 carbon atoms; 2-tetrahydrofurylmethyl or 2-furylmethyl, useful as analgesic agents.

16 Claims, No Drawings

2-(3-M-HYDROXY-PHENYL-1-SUBSTITUTED-3-PYRROLIDINYL)-ETHANOLS

The present invention relates to 2-(3-m-hydroxyphenyl-1-substituted-3-pyrrolidinyl)-ethanol derivatives.

More particularly, this invention provides compounds of formula I,

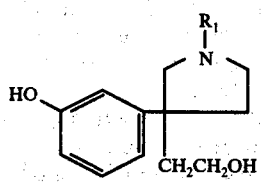

wherein $R_1$ is alkyl of 4 to 8 carbon atoms; cycloalkyl of 4 to 6 carbon atoms; phenethyl or phenethyl monosubstituted in the phenyl residue with fluorine, chlorine, bromine, methoxy or alkyl of 1 to 4 carbon atoms; 2-tetrahydrofurylmethyl or 2-furylmethyl.

When $R_1$ is alkyl, this may be either a branched or an unbranched moiety. The alkyl group preferably contains from 4 to 6 carbon atoms, especially 5 carbon atoms.

$R_1$ can be phenethyl or phenethyl substituted in the phenyl residue. When the phenethyl is substituted in the phenyl residue, the preferred substituents are fluorine, chlorine and bromine, especially chlorine. The o-chlorophenethyl group is particularly preferred. The phenyl residue can also be substituted with methoxy. Alternatively, the phenyl residue can be substituted with alkyl of 1 to 4 carbon atoms.

$R_1$ can also be cyclobutyl, cyclopentyl or cyclohexyl.

The invention also provides a process for the production of a compound of formula I, comprising a. producing a compound of formula Ia,

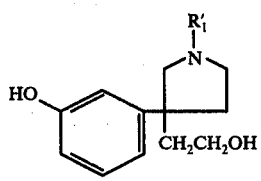

wherein
$R_1'$ has the same significance as $R_1$, as hereinbefore defined, with the exception of 2-furylmethyl, by hydrogenolysis of a compound of formula II,

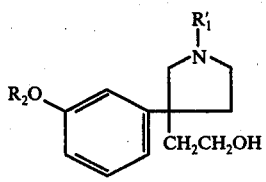

wherein
$R_1'$ as hereinbefore defined, and
$R_2$ is an ether protecting group which can be removed by hydrogenolysis, or b. producing a compound of formula Ib,

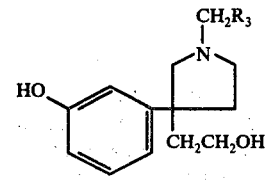

wherein
$R_3$ is alkyl of 3 to 7 carbon atoms, 2-tetrahydrofuryl, 2-furyl, benzyl or benzyl monosubstituted in the phenyl residue with fluorine, chlorine, bromine, methoxy or alkyl of 1 to 4 carbon atoms, by reducing a compound of formula III,

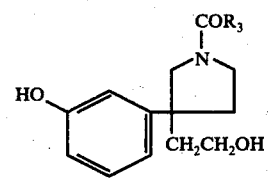

wherein
$R_3$ is as hereinbefore defined.

The removal of the ether protecting group by hydrogenolysis according to process variant a) can be effected by the usual methods for such splitting. A preferred removable ether protecting group is benzyl. The reaction may be effected in the presence of a catalyst and in the presence of an organic solvent which is inert under the reaction conditions. Suitable solvents include ethyl acetate, lower alcohols, for example methanol and ethanol. The reaction may suitably be effected at a temperature of from ca. 20° to 60° C and at a hydrogen pressure of from 1 to 200 atmospheres. Suitable catalysts include platinum-, nickel- or, preferably palladium catalysts. When $R_1'$, in the compounds of formula II, signifies chloro- or bromophenethyl, the halogen atoms may, in some instances, be replaced by hydrogen during the hydrogenolysis.

Process variant (b) can be effected according to the usual methods for the reduction of a keto group. For example, the reduction may be effected using suitable complex metal hydrides such as complex aluminium hydrides, for example lithium aluminium hydride, aluminium hydride and sodium dihydro-bis(2-methoxyethoxy)aluminate. Diborane can also be employed. The reduction may suitably be effected in an organic solvent which is inert under the reaction conditions. The reaction may conveniently be carried out at a temperature of from room temperature to the boiling temperature of the reaction mixture.

The resulting compounds of formula I may be isolated and purified using conventional techniques.

Free base forms of the compounds of formula I may be converted into salt forms, including acid addition salt forms, and vice versa in conventional manner.

Insofar as the production of starting materials is not described, these are either known or may be produced in accordance with known processes, for example in manner analogous to the processes described in the Examples.

In the following non-limitative Examples, all temperatures are in degrees Centigrade.

EXAMPLE 1

2-(3-m-Hydroxyphenyl-1-pentyl-3-pyrrolidinyl)ethanol 24.7 g of 2-(3-m-benzyloxyphenyl-1-pentyl-3-pyrrolidinyl)ethanol are hydrogenated with 2.5 g of palladium on carbon (10%) in 500 ml of methanol at 50° and at a hydrogen pressure of 5 atmospheres for 3 hours. At the end of the reaction period, the mixture is filtered and the clear filtrate evaporated. The crude title compound remains as a light yellow oil (12.9 g) which crystallizes. M.P. 116°–118°. The hydrochloride is obtained by the addition of an ethanolic solution of hydrogen chloride to an ethanolic solution of the title compound. M.P. 139°–140°.

The starting material can be obtained as follows:

a. 20 g of 3-m-methoxyphenyl-5-oxo-3-pyrrolidine acetic acid are dissolved in 100 ml of glacial acetic acid and 20 g of 63% hydrobromic acid, and boiled at reflux for 7 hours. The clear yellow reaction solution is evaporated and then 100 ml of water are added. The 3-m-hydroxyphenyl-5-oxo-3-pyrrolidine acetic acid crystallizes. M.P. 193°–195°.

b. 20 g of 3-m-hydroxyphenyl-5-oxo-pyrrolidine acetic acid are dissolved in 200 ml of ethanol, and then 6.8 g of sodium hydroxide are added. A solution of 29.1 g of benzyl bromide in 200 ml of ethanol is added in drops at room temperature over the course of 20 minutes to the suspension formed, whereupon the reaction solution becomes clear. The solution is further stirred at room temperature for 2½ hours. The crystallisate formed is filtered off, washed with a little ethanol/ether (5 : 95%) and dried. M.P. of the 3-m-benzyloxyphenyl-5-oxo-3-pyrrolidine acetic acid: 260°–265°.

c. 2-(3-m-benzyloxophenyl-3-pyrrolidinyl)ethanol is produced by the reduction of 25 g of 2-(3-m-benzyloxyphenyl-5-oxo-3-pyrrolidine) acetic acid with 5.85 g of lithium aluminium hydride in 500 ml of anhydrous tetrahydrofuran over a period of 20 hours at reflux temperature. After decomposing the excess reducing agent with water/tetrahydrofuran (1 : 1) in the cold, the liquid is filtered from the resultant hydroxide sediment, which is boiled out twice, each time with 200 ml of tetrahydrofuran. The combined clear tetrahydrofuran solutions are evaporated to dryness, the pH of the solution adjusted to 3 and the residue taken up in a little ethanol and hydrochloric acid. The hydrochloride form of the title compound is crystallized. M.P. 163°–168°.

d. 2-(3-m-Benzyloxyphenyl-1-pentyl-3-pyrrolidinyl)ethanol is prepared by reductive alkylation of 2-(3-m-benzyloxyphenyl-3-pyrrolidinyl)ethanol with n-valeraldehyde. The resulting oil is used without further purification.

EXAMPLE 2

2-[1-(2-Furylmethyl)-3-m-hydroxyphenyl-3-pyrrolidinyl]ethanol 8.45 g of lithium aluminium hydride in 150 ml of tetrahydrofuran are placed in a 500 ml sulphonation flask. A solution of 30 g of 2-[1-(2furoyl)-3-m-hydroxyphenyl-3-pyrrolidinyl]ethanol in 50 ml of tetrahydrofuran is added over a period of 45 minutes, as a result of which the temperature of the mixture rises to 65°. The mixture is boiled under reflux for 12 hours, cooled to 0° and the excess lithium aluminium hydride decomposed, with cooling, using water/tetrahydrofuran. The light green suspension is filtered, the residue boiled out 3 times using each time 200 ml of tetrahydrofuran and the combined tetrahydrofuran solutions evaporated under vacuum. 22 g of a pale yellow oil remain which crystallise after chromatographic purification on keiselguhr. M.P. 88°–90°.

The starting material can be obtained as follows:

a. 13 g of 2-(3-m-Benzyloxyphenyl-3-pyrrolidinyl)ethanol (prepared as in Example 1) are dissolved in 80 ml of ethanol and a solution of 0.275 g of palladium(II) chloride and 0.195 g of sodium chloride in 10 ml of water are added. The mixture is cooled to 0° and a solution of 1 g of sodium borohydride in 10 ml of water (to which 1 drop of concentrated caustic soda solution has been added) added over a period of 20 minutes. The reaction mixture is brought to room temperature and stirred for 30 minutes. The pH of the mixture is adjusted to 4 with 4 ml of concentrated hydrochloric acid and hydrogenated for a period of 20 hours at 50° and under a hydrogen pressure of 5 atmospheres. After filtration, the remaining pale yellow solution is evaporated. Crude 2-(3-m-hydroxyphenyl-3-pyrrolidinyl)ethanol, in the form of the hydrochloride, remains, which is used without further purification.

b. 18.5 g of 2-(3-m-Hydroxyphenyl-pyrrolidinyl)ethanol in a round-bottomed flask are dissolved in 100 ml of pyridine. 25.8 g of furan-2-carboxylic acid chloride are added, with stirring, over a period of 20 minutes at room temperature. The solution becomes dark, the temperature rises to 48°. Stirring is subsequently effected for 2 hours at room temperature followed by quenching in 500 ml of water. The resulting emulsion is extracted five times, each time with 100 ml of chloroform. The combined chloroform extracts are dried over magnesium sulphate and, after filtration, evaporated. The 2-[1-(2-furoyl)-3-m-hydroxyphenyl-3-pyrrolidinyl]ethanol remains as a dark oil and is used without further purification.

The following compounds can be prepared in manner analogous to Examples 1 and 2, using appropriate starting materials in approximately equivalent amounts.

| Ex. No. | R₁ | M.P. |
|---|---|---|
| 3 |  | Hydrochloride: 190–192° |
| 4 | —(CH₂)₃—CH₃ | 103–105° |
| 5 | CH₃<br>\|<br>—CH—CH₂—CH₃ | Naphthalene-1,5-disulphonate: 186–188° |
| 6 | —CH₂—CH(CH₃)₂ (—CH₂—CH⟨CH₃/CH₃) | Naphthalene-1,5-disulphonate: 214–216° |
| 7 | CH₃<br>\|<br>—CH₂—C—CH₃<br>\|<br>CH₃ | Hydrochloride: 184–186° |
| 8 |  | Hydrochloride: 198–200° |
| 9 |  | Hydrochloride: 162–164° |
| 10 | —CH₂— 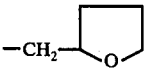 | 99–101° |
| 11 | —CH₂—CH₂—  —OCH₃ | Hydrochloride: 150–152° |

-continued

| Ex. No. | R₁ | M.P. |
|---|---|---|
| 12 | 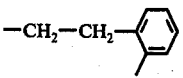 —CH₂—CH₂—(phenyl-Cl) | Hydrochloride: 199–201° |
| 13 | —(CH₂)₅—CH₃ | Hydrochloride: 140–142° |
| 14 | —(CH₂)₇—CH₃ | Hydrochloride: 138–140° |

The compounds of formula I are useful because they possess pharmacological activity in animals. In particular, the compounds are useful as analgesic agents for the treatment of pain as indicated in standard tests, e.g. in the phenyl-p-benzoquinone syndrome test in mice on p.o. administration of from 1 to 60 mg/kg animal body weight of the compounds, in the Randall-Selitto test in rats on s.c. administration of from 5 to 200 mg/kg animal body weight of the compounds, and in the shock titration test in the rhesus monkey on s.c. and p.o. administration of from 1 to 100 mg/kg animal body weight of the compounds.

For this use the dosage will, of course, vary depending on the compound employed, mode of administration and treatment desired. However, in general, satisfactory results are obtained when administered at a daily dosage of from 1 to 200 mg/kg animal body weight, conveniently given in divided doses 2 to 4 times a day or in sustained release form. For the large animals, the total daily dosage is in the range of from 100 to 400 mg, and dosage forms suitable for oral administration comprise from 25 mg to 200 mg of the compounds admixed with a solid or liquid pharmaceutical carrier or diluent.

The compounds may be administered in pharmaceutically acceptable salt forms, including phenolates and acid addition salt forms. Such salt forms exhibit the same order of activity as the free base forms and are readily prepared in conventional manner. Representative acids for acid addition salt forms include organic acids such as naphthalene-1,5-disulphonic acid and maleic acid and mineral acids such as hydrochloric acid. Suitable bases for phenolate formation include alkali metal hydroxides. The present invention also provides a pharmaceutical composition comprising a compound of formula I, in free base form or in pharmaceutically acceptable salt form, in association with a pharmaceutically acceptable carrier or diluent. Such compositions may be in the form of, for example, a solution or a capsule.

In one group of compounds, R₁ is alkyl of 4 to 7 carbon atoms, cycloalkyl of 4 to 6 carbon atoms, 2-tetrahydrofurylmethyl or 2-furylmethyl.

In a second group of compounds, R₁ is alkyl of 4 to 7 carbon atoms, 2-tetrahydrofurylmethyl or 2-furylmethyl.

What is claimed is:

1. A compound of formula I,

wherein
R₁ is alkyl of 4 to 8 carbon atoms; cycloalkyl of 4 to 6 carbon atoms; phenethyl or phenethyl monosubstituted in the phenyl residue with fluorine, chlorine, bromine, methoxy or alkyl of 1 to 4 carbon atoms, or a pharmaceutically acceptable salt form thereof.

2. A compound of claim 1 in which R₁ is n-pentyl.

3. A compound of claim 1 in which R₁ is

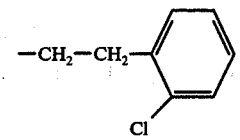

4. A method of treating pains in animals which comprises administering to an animal in need of such treatment a therapeutically effective amount of a compound of claim 1.

5. A pharmaceutical composition for use in the treatment of pains which comprises an analgesic effective amount of a compound of claim 1 in association with a pharmaceutically acceptable carrier or diluent.

6. The compound of claim 1 which is 2-(3-m-hydroxyphenyl-1-pentyl-3-pyrrolidinyl)-ethanol.

7. The compound of claim 1 wherein R₁ is

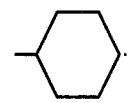

8. The compound of claim 1 wherein R₁ is —(CH₂)₃—CH₃.

9. The compound of claim 1 wherein R₁ is

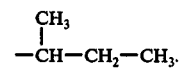

10. The compound of claim 1 wherein R₁ is

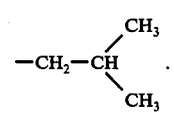

11. The compound of claim 1 wherein R₁ is

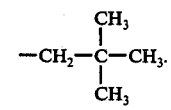

12. The compound of claim 1 wherein R₁ is

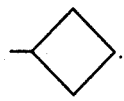

13. The compound of claim 1 wherein R₁ is

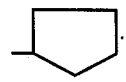

14. The compound of claim 1 wherein $R_1$ is
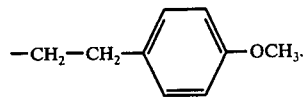
15. The compound of claim 1 wherein $R_1$ is $-(CH_2)_5-CH_3$.
16. The compound of claim 1 wherein $R_1$ is $-(CH_2)_7-CH_3$.
* * * * *